US010130624B2

(12) United States Patent
Vithalapuram et al.

(10) Patent No.: US 10,130,624 B2
(45) Date of Patent: Nov. 20, 2018

(54) PHARMACEUTICAL COMPOSITIONS OF AMLODIPINE AND BENAZEPRIL

(75) Inventors: Veena Vithalapuram, Maharashtra (IN); Vijaya Kumar Thommandru, Maharashtra (IN); Himadri Sen, Maharashtra (IN)

(73) Assignee: LUPIN LIMITED, Pune (IN)

( * ) Notice: Subject to any disclaimer, the term of this patent is extended or adjusted under 35 U.S.C. 154(b) by 1192 days.

(21) Appl. No.: 11/886,354

(22) PCT Filed: Jan. 25, 2006

(86) PCT No.: PCT/IN2006/000026
§ 371 (c)(1),
(2), (4) Date: Nov. 1, 2007

(87) PCT Pub. No.: WO2006/097943
PCT Pub. Date: Sep. 21, 2006

(65) Prior Publication Data
US 2008/0194542 A1 Aug. 14, 2008

(30) Foreign Application Priority Data
Mar. 15, 2005 (IN) .................. 0284/MUM/2005

(51) Int. Cl.
A61K 31/455 (2006.01)
A61K 31/55 (2006.01)
A61K 9/48 (2006.01)
A61K 9/50 (2006.01)

(52) U.S. Cl.
CPC .......... *A61K 31/455* (2013.01); *A61K 9/4808* (2013.01); *A61K 9/4858* (2013.01); *A61K 9/5084* (2013.01); *A61K 31/55* (2013.01)

(58) Field of Classification Search
USPC ....................................................... 514/183
See application file for complete search history.

(56) References Cited

U.S. PATENT DOCUMENTS

| | | | |
|---|---|---|---|
| 6,096,339 A | 8/2000 | Ayer et al. | |
| 6,162,802 A | 12/2000 | Papa et al. | |
| 6,482,841 B1 | 11/2002 | Letelier et al. | |
| 6,632,180 B1 * | 10/2003 | Laragh | 600/481 |
| 6,919,087 B2 | 7/2005 | Lemmens et al. | |
| 8,158,146 B2 * | 4/2012 | Kadosh et al. | 424/464 |
| 2002/0176889 A1 | 11/2002 | Lemmens et al. | |
| 2003/0022922 A1 | 1/2003 | Lemmens et al. | |
| 2003/0114497 A1 | 6/2003 | Alani et al. | |
| 2003/0139455 A1 * | 7/2003 | Ettema et al. | 514/355 |
| 2005/0019395 A1 | 1/2005 | Pragai et al. | |

FOREIGN PATENT DOCUMENTS

| | | |
|---|---|---|
| WO | WO 01 74390 | 10/2001 |
| WO | WO 02 49645 | 6/2002 |
| WO | WO 02 49646 | 6/2002 |
| WO | WO 2004/058711 | 7/2004 |
| WO | WO 2004/075825 | 9/2004 |
| WO | WO 2006 085208 | 8/2006 |
| WO | WO 2007 040511 | 4/2007 |

OTHER PUBLICATIONS

Lotrel, Lotrel prescribing information by Novartis, 2003, accessed by Wayback or Web.archive.org, pp. 1-17, https://web.archive.org/web/20030613220642/http://www.pharma.us.novartis.com/product/pi/pdf/lotrel.pdf, accessed Jul. 8, 2014.*
OrangeBookBlog, http://www.orangebookblog.com/2007/06/teva_defeats_no.html, accessed Feb. 9, 2014.*
K. Raghu Naidu et al., "Stability indicating RP-HPLC method for simultaneous determination of amlodipine and benazepril hydrochloride from their combination drug product", Journal of Pharmaceutical and Biomedical Analysis, New York, NY, US, vol. 39, No. 1-2, Sep. 1, 2005 (Sep. 1, 2005), pp. 147-155, XP005013202 ISSN: 0731-7085.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Complaint filed Dec. 12, 2006.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Answer and Counterclaim filed Jan. 19, 2007.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Novartis' Reply to the Answer and Counterclaim of Lupin Ltd. and Lupin Pharmaceuticals, Inc. filed Feb. 13, 2007.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, First Amended Answer and Amended Counterclaim filed Nov. 5, 2007.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Novartis' Reply to the Amended Counterclaims of Lupin Ltd. and Lupin Pharmaceuticals, Inc. filed Dec. 4, 2007.
*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Lupin's Reply Claim-Construction Brief filed Oct. 8, 2008.

(Continued)

*Primary Examiner* — Jeffrey S Lundgren
*Assistant Examiner* — Meghan Finn
(74) *Attorney, Agent, or Firm* — The Dobrusin Law Firm, PC

(57) ABSTRACT

A stable pharmaceutical composition consisting of (a) benazepril, in free or pharmaceutically acceptable salt form; and (b) amlodipine, in free or pharmaceutically acceptable salt form. The composition is free of alkali and alkaline earth metal carbonates and phosphates. The composition is also free of excipients which increase the pH of microenvironment above 5. It is therefore not required to physically separate the two drugs from each other.

21 Claims, No Drawings

(56) References Cited

OTHER PUBLICATIONS

*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Novartis' Response to Lupin's Opening Claim Construction Brief filed Oct. 8, 2008.

*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Opinion and Order filed Mar. 18, 2009.

*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Brief in Support of Lupin's Motion for Summary Judgment of Noninfringement filed Jul 2, 2009.

*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Statement of Uncontested Material Facts in Support of Lupin's Motion for Summary Judgment on Noninfringement filed Jul. 2, 2009.

*Novartis Corporation, Novartis Pharmaceuticals Corporation and Novartis International AG* v. *Lupin Ltd. and Lupin Pharmaceuticals, Inc.*, United States District Court for the District of New Jersey Civil Action No. 06-5954, Joint Stipulated Order of Dismissal filed Sep. 9, 2009.

"Impurities in New Medicinal Products", The European Agency for the Evaluation of Medicinal Products Human Medicine Evaluation Unit, Nov. 6, 1996, pp. 1-9, ICH Technical Coordination, London.

"Specifications: Test Procedures and Acceptance Criteria for New Drug Substances and New Drug Products: Chemical Substances", European Medicines Agency, May 2000, pp. 1-32, EMEA, London.

"Stability Testing of New Drug Substances and Products", European Medicines Agency, Aug. 2003, pp. 1-20, EMEA, London.

"Q3B(R) Impurities in New Drug Products", Guidance for Industry, U.S. Dept. of Health and Human Services—Food and Drug Administration, Nov. 2003, pp. 1-15, ICH.

"Q1A(R2) Stability Testing of New Drug Substances and Products", Guidance for Industry, U.S. Dept. of Health and Human Services—Food and Drug Administration, Nov. 2003, pp. 1-22, ICH.

"ANDAs: Impurities in Drug Products", Guidance for Industry, U.S. Dept. of Health and Human Services—Food and Drug Administration, Aug. 2005, pp. 1-8, OGD.

"ICH Harmonised Tripartite Guideline: Impurities in New Drug, Products: Q3B(R2)", International Conference on Harmonisation of Technical Requirements for Registration of Pharmaceuticals for Human Use, Jun. 2, 2006, pp. 1-12, ICH.

Beresford et al., "Metabolism of amlodipine in the rat and the dog: a species difference", Xenobiotica The Fate of Foreign Compounds in Biological Systems, Feb. 1988, pp. 169-182, 18:2, Taylor & Francis, London.

Beresford et al., "Metabolism and kinetics of amlodipine", Xenobiotica The Fate of Foreign Compounds in Biological Systems, Feb. 1988, pp. 245-254, 18:2, Taylor & Francis, London.

Nicholls, "Age, Diuretics, and Hypertension", J. Cardiovasc. Pharmacol, 1988, pp. S55-S59, 12:Suppl. 8, Raven Press.

Beresford et al., "Biotransformation of Amlodipine: Identification and synthesis of metabolites found in rat, dog and human urine/ Confirmation of structures by gas chromatography-mass spectrometry and liquid chromatography-mass spectrometry", Arzneim.-Forsch./Drug Res. 1989, pp. 201-209, 39(I):Nr 2, Kent, United Kingdom.

Physician's Desk Reference, 1992, pp. 408, 872,873-874, Medical Economics Data, Montvale, New Jersey.

Ragno et al.,"Photodegradation monitoring of amlodipine by derivative spectrophotometry", J. Pharmaceutical and Biomedical Analysis, 2002, pp. 19-24, vol. 27, Elsevier.

Letter from Dept. of Health & Human Services to Novartis Pharmaceuticals Corp., Aug. 29, 2003.

"Amlodipine Besilatc", European Pharmacopoeia 5.0, Jan. 2005, pp. 981-983, vol. 1. Council of Europe, Strasbourg.

"Official Monographs", U.S. Pharmacopoeia, 2012, pp. 2185-2188; 2312-2315, vol. 2, U.S. Pharmacopeial Convention, Rockville, MD.

Sweetman, Martindale The Complete Drug Reference $33^{rd}$ Ed., 2002, pp. 820-825: 843, Pharmaceutical Press, 2002.

\* cited by examiner

PHARMACEUTICAL COMPOSITIONS OF AMLODIPINE AND BENAZEPRIL

This application is a 371 of International Patent Application No. PCT/IN2006/000026 filed 25 Jan. 2006 which published as WO 2006/097943 on 21 Sep. 2006 and claims priority to Indian Patent Application No. 0284/MUM/2005 filed 15 Mar. 2005, the disclosures of which are incorporated by reference.

FIELD OF THE INVENTION

The present invention relates to stable pharmaceutical compositions of amlodipine, or its pharmaceutically acceptable salt and benazepril, or its pharmaceutically acceptable salt, characterized in that the two drugs are not physically separated from each other, further the said compositions are devoid of alkali and alkaline earth metal carbonates and phosphates.

BACKGROUND OF THE INVENTION

Calcium channel blockers (CCBs) and angiotensin converting enzyme inhibitors (ACEIs) are widely used for the treatment of hypertension and related diseases and conditions.

Amlodipine, a calcium channel blocker, and its salts are disclosed in U.S. Pat. No. 4,879,303. Further the maleate salt of amlodipine as set forth in U.S. Pat. No. 4,572,909.

Benazepril, an angiotensin converting enzyme inhibitor, its salts and benazepril at are disclosed in U.S. Pat. No. 4,410,520.

U.S. Pat. No. 6,162,802 claims pharmaceutical composition consisting of amlodipine and benazepril such that the two drugs are physically separated from each other. In the specifications of this patent, the inventors disclose that physical separation of amlodipine and benazepril is necessary as they are incompatible substances. Physical separation of the two drugs has been shown to be achieved in a number of ways; coating pellets of one active, before incorporating into a tablet of the other, separately coating pellets of each active and then filling in a capsule, coating pellets of one active and filling in a capsule with powder of the other active, microencapsulating each active separately in order to ensure that the two drugs do not come in contact and then blending together for use in a tablet or capsule, use of a dual or multiple compartment transdermal device, etc.

Physical separation of the two components however, not only requires complicated processing, it also has inherent risks and complications. For example, chance contamination of one drug with the other during preparation would lead to degradation products. Therefore a need was felt to find ways to over come the problem using alternate means of stabilization.

It has now been surprisingly found that a stable composition of a combination of amlodipine and benazepril can be prepared using excipients other than alkali and alkaline earth metal carbonates and phosphates, resulting in a product, which shows improved stability, thus avoiding the need of physical separation of the two drugs.

OBJECT OF THE INVENTION

It is therefore the principal object of the invention to prepare a stable pharmaceutical composition of amlodipine or its pharmaceutically acceptable salt and benazepril or its pharmaceutically acceptable salt, characterized in that the two drugs are not physically separated from each other.

It is another object of the invention to prepare a stable pharmaceutical composition of amlodipine or its pharmaceutically acceptable salt and benazepril or its pharmaceutically acceptable salt, which prevents degradation of the two drugs, using excipients other than alkali and alkaline earth metal carbonates and phosphates.

It is yet another object of the invention to prepare a stable pharmaceutical composition of amlodipine or its pharmaceutically acceptable salt and benazepril or its pharmaceutically acceptable salt, which prevents degradation of the two drugs, such that the pH of the microenvironment is below 5.

SUMMARY OF THE INVENTION

The present invention thus relates to a stable pharmaceutical composition consisting of (a) benazepril, in free or pharmaceutically acceptable salt form; and (b) amlodipine, in free or pharmaceutically acceptable salt form, characterized in that the two drugs are not physically separated from each other. The stabilization is achieved by using excipients other than alkali and alkaline earth metal carbonates and phosphates and those excipients, which increase the pH of microenvironment above 5.

DETAILED DESCRIPTION OF THE INVENTION

The invention relates to stabilized pharmaceutical compositions of amlodipine or its pharmaceutically acceptable salt, and benazepril and its pharmaceutically acceptable salt, which is prevented from degradation by avoiding the use of excipients selected from alkali and alkaline earth metal carbonates and phosphates. The composition is also stabilized by avoiding excipients, which raise the pH of the microenvironment above 5. The composition so prepared need not have the two drugs physically separated from each other.

Amlodipine as used herein refers to amlodipine in free or its pharmaceutically acceptable salt form.

Benazepril as used herein refers to benazepril in free or its pharmaceutically acceptable salt form.

Alkali and alkaline earth metal carbonates referred to in the present specification include sodium carbonate, sodium bicarbonate, calcium carbonate, magnesium carbonate, sodium phosphate, calcium phosphate, and calcium phosphate anhydrous.

Excipients, which raise the pH above 5, include sodium bicarbonate, sodium carbonate, meglumine and the like.

Destabilizing effect of these excipients was observed during preformulation studies. The studies were carried out by blending amlodipine & benazepril and then mixing with excipients in amounts intended to be used in the proposed compositions. For example, amlodipine:benazepril:diluent were blended in the ratio 0.7:1:10, amlodipine:benazepril:disintegrant were blended in the ratio 0.7:1:2, amlodipine:benazepril:binder were blended in the ratio 0.7:1:2, and amlodipine:benazepril:lubricant were blended in the ratio 0.7:1:0.5. The mixture was then exposed to accelerated stability conditions of 40° C. & 75% RH. The preformulation samples were observed for physical changes such as change in the colour of blend. Samples, which otherwise did not show change in color, were analyzed for degradation products of amlodipine and benazepril using validated HPLC method.

During the study it was observed that sodium carbonate, sodium bicarbonate, sodium phosphate dibasic, sodium phosphate tribasic, calcium carbonate, dibasic calcium phosphate, magnesium carbonate, meglumine and polyethylene glycol showed changes in color of the blend from white to cream colored, yellowish, light brown or dark brown.

It was observed that amlodipine:benazepril combination may be incompatible with alkali and alkaline earth metal carbonates and phosphates. It was also observed that excipients, which increase the pH of the blend above 5, resulted in color change of the preformulation blend. These included meglumine, besides alkali and alkaline earth metal carbonates and phosphates.

Results of samples which were analyzed for impurities are summarized in tables 1(a), 1(b) and 1(c).

TABLE 1 (a)

Preformulation compatibility study where incompatibility was found Amlodipine:benazepril:diluent were mixed in the ratio of 0.7:1:10, amlodipine:benazepril:disintegrant were mixed in the ratio of 0.7:1:2, amlodipine:benazepril:binder were mixed in the ratio of 0.7:1:2, and amlodipine:benazepril:lubricant were mixed in the ratio of 0.7:1:0.5 and kept at 40° C. & 75% RH for one month. The samples were analyzed for degradation products.

| | Excipients | | | | | |
|---|---|---|---|---|---|---|
| Related substances | Dibasic Calcium Phosphate (0.7:1:10) | | Sodium Stearyl Fumarate (0.7:1:0.5) | | Sodium Starch Glycolate (0.7:1:2) | |
| (%) | Initial | 1M | Initial | 1M | Initial | 1M |
| Amlodipine impurity D | 1.869 | 12.759 | 0.000 | 0.000 | 0.000 | 0.000 |
| Benazepril impurity C | 0.945 | 16.786 | 1.107 | 3.517 | 1.017 | 4.116 |
| Benazepril impurity G | 0.052 | 0.576 | 0.076 | 0.088 | 0.000 | 0.000 |
| Total impurities | 3.923 | 44.146 | 1.738 | 4.090 | 1.299 | 4.451 |

It was observed that the two drug combination was unstable in the presence of dibasic calcium phosphate, sodium stearyl fumarate and sodium starch glycolate.

TABLE 1 (b)

Preformulation compatibility study where no excipients incompatibility was found

| | Excipients | | | | | | | |
|---|---|---|---|---|---|---|---|---|
| Related substances | Mannitol (0.7:1:10) | | Lactose (0.7:1:10) | | Crospovidone (0.7:1:2) | | Microcrystalline cellulose (0.7:1:10) | |
| (%) | Initial | 1M | Initial | 1M | Initial | 1M | Initial | 1M |
| Amlodipine impurity D | 0.000 | 0.069 | 0.000 | 0.000 | 0.000 | 0.000 | 0.000 | 0.000 |
| Benazepril impurity C | 0.205 | 0.286 | 0.245 | 0.263 | 0.197 | 0.193 | 0.314 | 0.617 |
| Benazepril impurity G | 0.067 | 0.046 | 0.000 | 0.000 | 0.000 | 0.000 | 0.000 | 0.000 |
| Total impurities | 0.767 | 1.167 | 0.551 | 0.551 | 0.519 | 0.496 | 0.490 | 0.887 |

The two drug combination was stable in combination with mannitol, lactose, crospovidone and microcrystalline cellulose.

TABLE 1 (c)

Preformulation compatibility study
The two drugs were blended together without any excipients and charged on stability.

| Related substances | Benazepril alone | | Amlodipine alone | | Amlodipine + Benazepril (0.7:1.0) | |
|---|---|---|---|---|---|---|
| (%) | Initial | 3M | Initial | 3M | Initial | 3M |
| Amlodipine impurity D | 0.000 | 0.000 | 0.000 | 0.000 | 0.000 | 0.010 |
| Benazepril impurity C | 0.130 | 0.143 | 0.000 | 0.000 | 0.101 | 0.114 |
| Benazepril impurity G | 0.060 | 0.000 | 0.000 | 0.000 | 0.040 | 0.039 |
| Total impurities | 0.260 | 0.267 | 0.130 | 0.143 | 0.240 | 0.261 |

Surprisingly, contrary to prior art disclosures we have found that amlodipine and benazepril are not incompatible but are unstable when together only in the presence of certain excipients and pH conditions.

Pharmaceutical compositions were prepared by avoiding the excipients, which degrade the two-drug combination. These compositions may be in the form of uncoated tablets of one drug and powder blend of the other, filled into capsules; uncoated granules of one drug and powder blend of the other, filled into capsules; uncoated granules of two drugs either filled into capsules or compressed into tablets; powder blends of the two drugs filled into capsules; uncoated beads of the two drugs filled into capsules; microtablets of the two drugs filled into capsules and the like.

The stable pharmaceutical compositions further comprise excipients selected from the group comprising pharmaceutically acceptable diluents, binders, disintegrants and lubricants, well known to those skilled in the art.

Diluents referred to in the present invention include one or more selected from mannitol, lactose, dextrose, xylitol, sorbitol, sucrose, microcrystalline cellulose, starch, pregelatinized starch and the like known to a person skilled in the art.

Disintegrants referred to in the present invention preferably include superdisintegrant type being well known to a person skilled in the art. As examples of these disintegrants the following can be mentioned: cross linked polyvinylpyrrolidones, modified starches, particularly sodium starch glycolate, and glycolis low pH, modified celluloses, insoluble cation exchange resins and L-HPC (low substituted hydroxypropyl cellulose).

Croscarmellose sodium is commercialized under the trade name Ac-Di-Sol and sodium starch glycolate under the trade names primojel and explotab, kollidon CL and polyplasdone XL are commercial crospovidone products.

Binders referred to in the present invention include those well known to a person skilled in the art, as exemplified can be celluloses such as hydroxypropyl cellulose, hydroxy ethyl cellulose, ethyl cellulose, hydroxypropyl methylcellulose, methylcellulose or mixtures thereof, acrylates, methacrylates, povidone and other materials known to have cohesive and desirable binding properties.

Lubricants referred to in the present invention include those well known to a person skilled in the art, as exemplified can be calcium stearate, magnesium stearate, sodium stearyl fumarate, talc, colloidal silicon dioxide, palmitic acid, carnauba wax, glyceryl monostearate, hydrogenated castor oil, polyoxyethylene monostearates, fats and stearic acid or mixtures thereof.

The pharmaceutical composition consisting of benazepril and amlodipine may be in the form of a tablet or a capsule prepared by blending the two drugs with excipients, granulating them separately and mixing without coating the granules, tabletting one active and blending with powder or granules of another. The formulation uses techniques well known to those skilled in the art such as direct compression, wet granulation, dry granulation, layering, pelletization etc. The compositions are characterized in that the two drugs are not physically separated from each other.

Formulations prepared above were analyzed for pH. Each composition equivalent to one dose of amlodipine and benazepril was dispersed in 20 ml of water and pH of resulting dispersion was measured. pH data of these formulations is summarized in table 3.

The following examples are illustrative of the present invention, and the examples should not be considered as limiting the scope of this invention in any way, as these examples and other equivalents thereof will become apparent to those versed in the art, in the light of the present disclosure, and the accompanying claims.

Various formulation trials were carried out using excipients, which were found to be compatible with the two-drug combination. These included preparation of uncoated tablet of one drug and filling into hard gelatin capsule with powder blend of the other. The tablet may be prepared by wet or dry method. Alternately granules of one drug may be filled into capsules with powder blend of the other or the two drugs may be blended and filled into hard gelatin capsules.

EXAMPLE 1

Capsules containing Benazepril (20 mg) as uncoated tablet and Amlodipine (10 mg) in powder form

| Sr. No. | Ingredients | mg/Capsule |
|---|---|---|
| 1. | Benazepril Hydrochloride | 20.0 |
| 2. | Lactose | 16.0 |
| 3. | Microcrystalline cellulose | 9.0 |
| 4. | Povidone | 1.0 |
| 5. | Crospovidone | 2.0 |
| 6. | Hydrophobic silica | 1.0 |
| 7. | Magnesium stearate | 1.0 |
| 8. | Isopropyl alcohol for granulation | Lost in processing |

Mix benazepril hydrochloride, lactose, microcrystalline cellulose and crospovidone, granulate with povidone solution in isopropyl alcohol and dry the granules.
Mix the granules with crospovidone, hydrophobic silica, magnesium stearate and compress into tablets using suitable tooling.

| 9. | Amlodipine Besylate | 14.07 |
|---|---|---|
| 10. | Microcrystalline cellulose | 79.93 |
| 11. | Crospovidone | 4.0 |
| 12. | Magnesium Stearate | 2.0 |

Mix amlodipine besylate, microcrystalline cellulose and crospovidone and lubricate the blend with magnesium stearate.

Fill the final blend of amlodipine and uncoated tablet of benazepril into capsules.

EXAMPLE 2

Capsules containing Benazepril (20 mg) as uncoated tablet and Amlodipine (10 mg) in powder form, prepared by dry processing

| Sr. No. | Ingredients | mg/Capsule |
|---|---|---|
| 1. | Benazepril Hydrochloride | 20.0 |
| 2 | Lactose | 43.0 |
| 3. | Microcrystalline cellulose | 10.0 |
| 4. | Crospovidone | 2.0 |
| 5. | Colloidal silicon dioxide | 1.0 |
| 6. | Hydrogenated Castor Oil | 4.0 |

Mix benazepril hydrochloride, lactose, crospovidone, colloidal silicon dioxide and hydrogenated castor oil and directly compress the blend into tablets using suitable tooling.

| 7. | Amlodipine Besylate | 14.07 |
|---|---|---|
| 8. | Microcrystalline cellulose | 180.93 |
| 9. | Crospovidone | 4.0 |
| 10. | Magnesium stearate | 2.0 |

Mix amlodipine besylate, microcrystalline cellulose and crospovidone, and lubricate the blend with magnesium stearate.

Fill the final blend of amlodipine and uncoated tablet of benazepril into Capsules.

EXAMPLE 3

Capsules containing granules of Benazepril (20 mg), and amlodipine (10 mg) powder were prepared as follows:

| Sr. No. | Ingredients | mg/Capsule |
|---|---|---|
| 1. | Benazepril Hydrochloride | 20.0 |
| 2. | Mannitol | 30.0 |
| 3. | Crospovidone | 4.0 |
| 4. | Ethyl cellulose | 0.2 |
| 5. | Isopropyl alcohol | Lost in processing |
| 6. | Hydrogenated castor oil | 2.0 |

Mix benazepril, mannitol, crospovidone and granulate with ethylcellulose dissolved in isopropyl alcohol. Dry the granules and lubricate with hydrogenated castor oil.

| 7. | Amlodipine Besylate | 14.07 |
|---|---|---|
| 8. | Mannitol | 126.73 |
| 9. | Crospovidone | 2.0 |
| 10. | Hydrophobic silica | 2.0 |
| 11. | Magnesium Stearate | 1.0 |

Mix amlodipine besylate, mannitol, crospovidone and hydrophobic silica, and lubricate with magnesium stearate.

Fill the benazepril granules and amlodipine blend into hard gelatin capsules.

EXAMPLE 4

Capsules containing benazepril (20 mg) and amlodipine (10 mg) by blending the two drugs.

| Sr. No. | Ingredients | mg/Capsule |
|---|---|---|
| 1. | Amlodipine Besylate | 14.07 |
| 2. | Benazepril Hydrochloride | 20 |
| 3. | Crospovidone | 6 |
| 4. | Mannitol | 156.73 |
| 5. | Hydrophobic silica | 2 |
| 6. | Magnesium Stearate | 1 |

Mix amlodipine besylate, benazepril hydrochloride, mannitol, hydrophobic silica and crospovidone. Lubricate the blend with magnesium stearate.

Fill the final blend of amlodipine and benazepril into capsules.

The formulations prepared according to the examples above were subjected to stability studies at accelerated conditions of temperature and humidity of 40° C. and 75% RH for one month. Results of these stability studies are summarized in table 2 below.

TABLE 2

Stability Data

| Related substances | Example 1 Initial | Example 1 1M | Example 2 Initial | Example 2 1M | Example 3 Initial | Example 3 1M | Example 4 Initial | Example 4 1M |
|---|---|---|---|---|---|---|---|---|
| Amlodipine impurity D (%) | 0.000 | 0.000 | 0.045 | 0.048 | 0.000 | 0.030 | 0.035 | 0.029 |
| Benazepril impurity C (%) | 0.162 | 0.411 | 0.140 | 0.169 | 0.152 | 0.191 | 0.169 | 0.142 |
| Benazepril impurity G (%) | 0.057 | 0.000 | 0.052 | 0.000 | 0.000 | 0.000 | 0.000 | 0.000 |
| Total impurities (%) | 0.342 | 0.695 | 0.355 | 0.478 | 0.279 | 0.506 | 0.359 | 0.391 |

TABLE 3 pH Data for the formulations

| S. No. | Example No. | pH |
|---|---|---|
| 1 | Example 1, 2 | 3.21 |
| 2 | Example 3 | 3.16 |
| 3 | Example 4 | 3.13 |

As can be seen from examples 1 to 4, formulations containing amlodipine and benazepril not physically separated from each other can be stabilized with proper selection of pH and excipients.

The invention claimed is:

1. A stable pharmaceutical composition comprising (a) benazepril, in free or pharmaceutically acceptable salt form; and (b) amlodipine, in free or pharmaceutically acceptable salt form,
   characterized in that the benazepril and the amlodipine are not physically separated from each other and that the stable pharmaceutical composition is devoid of the following excipients:
   meglumine,
   polyethylene glycol,
   sodium stearyl fumarate and sodium starch glycolate, and
   alkali and alkaline earth metal carbonates and phosphates.

2. The stable pharmaceutical composition of claim 1, wherein the amlodipine is amlodipine besylate.

3. The stable pharmaceutical composition of claim 1, wherein the ratio of benazepril to amlodipine corresponds to a weight ratio of benazepril hydrochloride to amlodipine free base from 1:8 to 16:1.

4. The stable pharmaceutical composition of claim 1, wherein the amount of benazepril is from 5 mg to 160 mg benazepril hydrochloride.

5. The stable pharmaceutical composition of claim 1, wherein the amount of amlodipine is from 2.5 mg to 20 mg of amlodipine freebase.

6. The stable pharmaceutical composition of claim 1, which further comprises excipients selected from the group comprising diluents, binders, disintegrants and lubricants.

7. The stable pharmaceutical composition of claim 1, in the form of a capsule comprising within it (a) an uncoated tablet of benazepril, and (b) amlodipine powder.

8. The stable pharmaceutical composition of claim 1, in the form of a capsule comprising within it powder blends of amlodipine and benazepril.

9. The stable pharmaceutical composition of claim 1, in the form of a capsule comprising within it granules of benazepril and powder of amlodipine.

10. A process of preparing the stable pharmaceutical composition of claim 1, wherein at least one of the benazepril and the amlodipine is blended with excipients, wherein the benazepril and the amlodipine are granulated separately, wherein the granulated benazepril and amlodipine are mixed without coating the granules, and wherein the mixture is filled into capsules.

11. A process of preparing the stable pharmaceutical composition of claim 1, wherein at the least one of benazepril and the amlodipine is tableted and blended with powder or granules of the other of the benazepril and the amlodipine without coating the tablet and wherein the blend is filled into hard gelatin capsules.

12. A process of preparing the stable pharmaceutical composition of claim 1, wherein powder blends of both the benazepril and the amlodipine are mixed and filled into hard gelatin capsules.

13. A process of preparing the stable pharmaceutical composition of claim 1, wherein at least one of the benazepril and the amlodipine is blended with excipients, wherein the benazepril and the amlodipine are granulated separately, wherein the granulated benazepril and amlodipine are mixed without coating the granules, and wherein the mixture is compressed into tablets.

14. A process of preparing the stable pharmaceutical composition of claim 1, wherein powder blends of both the benazepril and the amlodipine are mixed and compressed into tablets.

15. The stable pharmaceutical composition of claim 1, wherein the benazepril is benazepril hydrochloride.

16. The stable pharmaceutical composition of claim 6, wherein the excipients are selected from the group consisting of mannitol, lactose, crospovidone and microcrystalline cellulose.

17. The stable pharmaceutical composition of claim 1, wherein after about 1 month at about 40° C. at about 75% relative humidity, the pharmaceutical composition contains:
   i) no more than about 0.411% of impurity C by weight relative to the benazepril; and/or
   ii) no more than about 0.048% of impurity D by weight relative to the amlodipine.

18. The pharmaceutical composition of claim 17, wherein the pharmaceutical composition is encapsulated.

19. The pharmaceutical composition of claim 17, wherein the benazepril is benazepril hydrochloride.

20. The pharmaceutical composition of claim 17, wherein the amlodipine is amlodipine besylate.

21. The pharmaceutical composition of claim 17, wherein the benazepril is prepared by wet granulation, and the amlodipine is prepared by dry processing.

* * * * *